(12) United States Patent
Bayon et al.

(10) Patent No.: US 8,679,779 B2
(45) Date of Patent: Mar. 25, 2014

(54) MEDICAL DEVICES WITH DEFINABLE POROSITY PRODUCED BY BACTERIAL POLYMER BIO-SYNTHESIS

(75) Inventors: Yves Bayon, Lyons (FR); Sébastien Ladet, Lyons (FR); Olivier Lefranc, Chatillon sur Chalaronne (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 254 days.

(21) Appl. No.: 13/125,647

(22) PCT Filed: Nov. 6, 2009

(86) PCT No.: PCT/IB2009/007658
§ 371 (c)(1),
(2), (4) Date: Jul. 11, 2011

(87) PCT Pub. No.: WO2010/052582
PCT Pub. Date: May 14, 2010

(65) Prior Publication Data
US 2011/0263841 A1    Oct. 27, 2011

Related U.S. Application Data

(60) Provisional application No. 61/112,295, filed on Nov. 7, 2008.

(51) Int. Cl.
| | | |
|---|---|---|
| C12N 15/52 | (2006.01) | |
| C12P 1/00 | (2006.01) | |
| C12Q 1/04 | (2006.01) | |

(52) U.S. Cl.
USPC .............................................. 435/41; 435/29

(58) Field of Classification Search
USPC ......................................................... 435/41
See application file for complete search history.

(56) References Cited

U.S. PATENT DOCUMENTS

| | | | |
|---|---|---|---|
| 2003/0064089 A1 | 4/2003 | Kumar | |
| 2007/0054880 A1* | 3/2007 | Saferstein et al. | 514/57 |
| 2011/0224703 A1* | 9/2011 | Mortarino | 606/151 |

FOREIGN PATENT DOCUMENTS

| | | |
|---|---|---|
| KR | 2003 0093009 | 12/2003 |
| WO | WO 00/34454 | 6/2000 |
| WO | WO 2007/027849 | 3/2007 |
| WO | WO 2007/064881 | 6/2007 |

OTHER PUBLICATIONS

Uraki, Y et al. "Honeycomb-like architecture produced by living bacteria, *Gluconacetobacter xylinus*" 2007 Carbohydrate Polymers 69 1-6.*
Morrice et al ."B-Agarase I and II from *Pseudomonas atlantica* substrate specificities" 1983 Eur, J. Biochem. 137, 149-154.*
International Search Report PCT/IB2009/007658 dated Feb. 15, 2010.
Uraki et al., "Honeycomb-like Architecture Produced by Living Bacteria", vol. 69, No. 1. Mar. 30, 2007, Abstract 1page.
Bäckdahl Henrik et al., "Engineering Microporosity in Bacterial Cellulose Scaffolds", vol. 2. No. 6, Aug. 2008, Abstract 1 page.

* cited by examiner

*Primary Examiner* — John S Brusca
*Assistant Examiner* — Gerard Lacourciere

(57) ABSTRACT

The present invention relates to a method of forming an implantable medical device comprising: culturing polymer-producing bacteria preferably *Acetobacter xylinum* in the presence of a degradable support; and removing the degradable support to recover an implant having pores of a configuration determined at least in part by the configuration of the degradable support. The invention also relates to a medical device obtained by such a method.

7 Claims, 1 Drawing Sheet

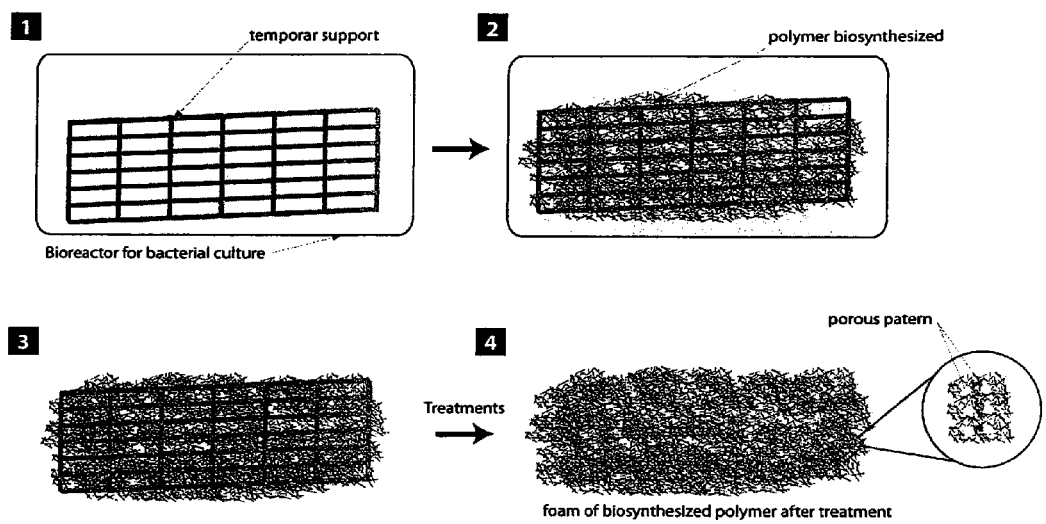
illustration of the process for design porous pattern within polymeric implant by biosynthesis.

MEDICAL DEVICES WITH DEFINABLE POROSITY PRODUCED BY BACTERIAL POLYMER BIO-SYNTHESIS

CROSS-REFERENCE TO RELATED APPLICATIONS

This application is a U.S. National Stage Application filed under 35 U.S.C. §371(a) of International Application No. PCT/IB2009/007658 filed Nov. 6, 2009, which claims the benefit of and priority to U.S. Provisional Application Ser. No. 61/112,295 filed Nov. 7, 2008, the entire contents of which are incorporated by reference herein.

Medical devices with tuneable porosity in accordance with the present disclosure include polymer biosynthesized by culturing bacteria in bioreactor.

An aspect of the present invention is a method of forming an implantable medical device comprising:

culturing polymer-producing bacteria in the presence of a degradable support; and removing the degradable support to recover an implant having pores of a configuration determined at least in part by the configuration of the degradable support.

In embodiments, the bacterial polymer is cellulose. The bacterial cellulose may be derived from *Acetobacter xylinum*. The bacterial cellulose may be further oxidized. The degradable support may comprise a textile made from multifilament yarns, monofilament yarns, or combinations thereof.

In embodiments, the degradable support is suspended at a distance of about 1 mm to about 3 mm above the bottom of a culture vessel during said culturing.

Another aspect of the present invention is an implantable medical device produced by the method described above.

Another aspect of the present invention is a method of treating a wound comprising contacting a wound with a medical device as described above.

The present disclosure at least in part, relates to methods for producing polymer foam/pellicles/films by culturing bacteria in culture vessels or bioreactors including dissolvable three dimensional ("3D") support materials on which or around which the bacteria can grow, proliferate and form an extracellular network of polymer as illustrated schematically in FIGS. 1A-D. As seen in FIG. 1A, a temporary support is placed within a bioreactor. The components necessary for culturing bacteria are then added to the bioreactor and polymer is biosynthesized by culturing the bacteria as shown in FIG. 1B. The resulting biopolymer-support composite is recovered as shown in FIG. 1C. Then, the biopolymer-support composite is further processed in a manner that removes the temporary support, leaving only the foam of biosynthesized polymer as shown in FIG. 1D.

The 3D-support materials can be made of any dissolvable or chemically degradable material that is compatible with the culture conditions, allowing the growth of the bacteria and having the characteristic of being able to be eliminated during the washing and purification process, to offer a pre-programmed porosity provided by the 3D-support material pattern/shape/architecture.

Suitable materials from which the degradable temporary support can be made include, but are not limited to poly(lactic acid) (PLA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers thereof and mixtures thereof. They are also preferably obtained from derivatives of polysaccharides among hyaluronic acid, alginic acid, poly (glucuronic acid), chitosan, chitin, cellulose preferentially cross-linked derivatives thereof and mixtures thereof.

In embodiments, the temporary support is a textile. Suitable textiles can be prepared using known methods such as weaving, braiding or knitting. The textile may be formed from multifilament yarns, monofilament yarns or any combination of thereof. The textiles can be three dimensional textiles, for example including for the latter spacers and the yarns are from dissolvable or chemically degradable materials or in any combinations of thereof. In embodiments, the temporary support may, for example, have an openwork three-dimensional ("3D") structure (see, e.g. U.S. Pat. No. 6,451,032, the entire disclosure of which is incorporated herein by this reference), and in particular a "honeycomb" structure, and thus a certain thickness which separates the two surfaces of the fabric. This textile can be obtained, for example, with a Rachel knit formed on a double needlebed. The spacing of the two needle beds and the delivery speeds of the yarns allow a finished textile to be obtained in three dimensions (three-dimensional structure), with a thickness of between 1 and 3 mm, and for example of about 1.8 mm, for a weight of less than about 100 g/m2.

The microbial cellulose may be produced as wet pellicles or films from bacteria that synthesize cellulose. Cellulose is synthesized by bacteria belonging to the genera *Acetobacter, Rhizobium, Agrobacterium*, and *Sarcina*. Cellulose may be produced by certain bacteria from glucose in the presence of oxygen, (such as, for example, *Acetobacter xylinum*, referenced hereinafter as the "bacteria"), in static conditions or in a bioreactor (see, e.g. U.S. Pat. Nos. 4,912,049 and 5,955,326, the entire disclosures of which are incorporated herein by this reference). Cellulose suitable for use in the present implants may be obtained by the fermentation of the bacteria. In embodiments, a derivative of the cellulose is employed, such as oxidized cellulose resulting from the oxidation of the cellulose by periodic acid or nitrogen dioxide.

Microbial cellulose possesses inherent characteristics which allow effective promotion of wound healing (see, e.g. U.S. Pat. No. 7,390,492, the entire disclosure of which is incorporated herein by this reference). In this regard, microbial cellulose displays properties (such as a multi-layer three dimensional laminar structure) that distinguish it from plant cellulose and other natural polymeric materials. In this regard, microbial cellulose shows excellent wet strength, does not easily breakdown under compression and demonstrates high moisture handling ability.

Microbial cellulose possesses inherent characteristics which allow effective promotion of wound healing (see, e.g., U.S. Pat. No. 7,390,492, the entire disclosure of which is incorporated herein by this reference). Microbial cellulose displays properties (such as unique multi-layer three dimensional laminar structures) that distinguish it from plant cellulose and other natural polymeric materials. Microbial cellulose shows excellent wet strength, does not easily breakdown under compression and demonstrates high moisture handling ability.

In static culture conditions of the bacteria, the temporary support can be laid at the bottom of the culture vessel or at a distance of 1 mm to 3 mm above the bottom of the vessel, fixed by any appropriate means. The temporary support can be fixed in such a way to give the desired shape of temporary support in the cellulose pellicle or film. For example, if the temporary support is a textile, it may be fixed with enough tension to remain substantially flat and parallel to the bottom of the vessel.

Suitable static conditions for culturing bacteria are disclosed in U.S. Pat. Nos. 4,912,049 and 5,955,326 in the description part and illustrated by the examples of these documents.

The material from which the degradable temporary support is made is selected from its ability to withstand the culture conditions, in an aqueous medium, at a temperature about 30° C., during several days, at a mild acid pH (pH in the range of 2 to 6). The material may also withstand the full product processing, including the depyrogenation step. For example, the depyrogenation step described in the US document 2007/0128243 A1 may be optimized by lowering the temperature and the sodium hydroxide concentration. In other embodiments, a step of the manufacturing process once the cellulose is harvested may help or fully contribute to the dissolution of the temporary support, such as the depyrogenation step, usually done at a high temperature and in a very alkaline medium (e.g., PLA, PGA, PLGA), as well as the drying step which may rely on the use of solvents which can both remove water and fully remove the temporary support by dissolution.

It is another embodiment of the present disclosure to obtain open cellulose sheets once they are implanted in vivo, after about 1 day to about several months, in embodiments after about 1 week to about 1 month. This can be obtained by adding a step in the purification process of the cellulose sheet, which can fragilize or partially degrade the temporary support.

The medical devices in accordance with this disclosure may be produced at a predetermined size or produced in large sheets which may be cut to sizes appropriate for the envisaged application. The medical devices may be packaged in single or dual pouches and sterilized using conventional techniques, such as, but not limited to, irradiation with beta (electronic irradiation) or gamma (irradiation using radioactive cobalt) rays at about 25 KGy to about 35 KGy, and/or sterilized by ethylene oxide. In embodiments where hydrolytically unstable materials are used in forming the devices, such as polyglycolic acid or polylactic acid, the devices can be packaged under sufficiently dry conditions to ensure that no degradation of the device takes place during storage.

It will be understood that various modifications may be made to the embodiments disclosed herein. Thus, those skilled in the art will envision other modifications within the scope and spirit of the disclosure.

The invention claimed is:

1. A method of forming an implantable medical device comprising:
   culturing polymer-producing bacteria in the presence of a degradable textile made from multifilament yarns, monofilament yarns, or combinations thereof; and
   removing the degradable textile to recover an implant having pores of a configuration determined at least in part by the configuration of the degradable textile.

2. A method as in claim 1, wherein the bacterial polymer is cellulose.

3. A method as in claim 2, wherein the bacterial cellulose is derived from *Acetobacter xylinum*.

4. A method as in claim 2, wherein the bacterial cellulose is further oxidized.

5. A method as in claim 1, wherein the degradable textile comprises multifilament yarns.

6. A method as in claim 1, wherein the degradable textile is suspended at a distance of about 1 mm to about 3 mm above the bottom of a culture vessel during said culturing.

7. An implantable medical device produced by the method of claim 1.

* * * * *